United States Patent [19]

Schraga

[11] Patent Number: 5,697,916
[45] Date of Patent: *Dec. 16, 1997

[54] HYPODERMIC DOSAGE MEASURING DEVICE

[75] Inventor: Steven Schraga, Surfside, Fla.

[73] Assignee: Stat Medical Devices Inc., Miami, Fla.

[*] Notice: The term of this patent shall not extend beyond the expiration date of Pat. No. 5,468,233.

[21] Appl. No.: 561,325

[22] Filed: Nov. 21, 1995

[51] Int. Cl.$^6$ ............................................. A61M 5/00
[52] U.S. Cl. .......................... 604/201; 604/155; 604/187
[58] Field of Search ........................ 604/207, 407, 604/403, 905, 155, 187; 128/DIG. 1; 141/27, 94

[56] References Cited

U.S. PATENT DOCUMENTS

| | | |
|---|---|---|
| 2,586,581 | 2/1952 | Tschischeck . |
| 2,861,570 | 11/1958 | Beecher . |
| 3,807,464 | 4/1974 | Pitesky . |
| 3,833,030 | 9/1974 | Waldbauer, Jr. et al. . |
| 3,875,979 | 4/1975 | Hults . |
| 3,907,009 | 9/1975 | Dobbins . |
| 4,018,223 | 4/1977 | Ethington . |
| 4,098,276 | 7/1978 | Bloom et al. . |
| 4,219,055 | 8/1980 | Wright . |
| 4,252,159 | 2/1981 | Maki . |
| 4,274,453 | 6/1981 | Lee . |
| 4,357,971 | 11/1982 | Friedman . |
| 4,434,820 | 3/1984 | Glass . |
| 4,475,915 | 10/1984 | Sloane . |
| 4,489,766 | 12/1984 | Montada . |
| 4,778,454 | 10/1988 | Ladow . |
| 4,883,101 | 11/1989 | Strong . |
| 5,468,233 | 11/1995 | Schraga . |

FOREIGN PATENT DOCUMENTS

| | | |
|---|---|---|
| 1026593 | 4/1966 | United Kingdom . |
| 1179888 | 2/1970 | United Kingdom . |

*Primary Examiner*—Manuel Mendel
*Attorney, Agent, or Firm*—Greenblum & Bernstein, P.L.C.

[57] ABSTRACT

A hypodermic dosage measuring device to be utilized with a hypodermic syringe and a conventional drug vial, the dosage measuring device including a vial holding portion adapted to hold a head of the drug vial non-slidably therein, a syringe holding portion adapted to hold the syringe in a non-slidable position with a needle of the syringe disposed within the drug vial, and a dose adjustment portion, the dose adjustment portion including an elongate plunger holder and gear element, the plunger holder and gear element each including a plurality of teeth thereon such that movement of the gear element results in an elongate track segment of the plunger holder sliding in a longitudinal direction parallel to a length of the syringe. The plunger holder further including a plunger engagement segment extending perpendicularly from the proximal end of the track segment, the plunger engagement section being adapted to engage a plunger of the syringe such that longitudinal movement of the plunger holder results in corresponding longitudinal movement of the plunger of the syringe relative to a dosage holding area of the syringe. The precise dosage measure is indicated by a digital display and/or an audible indicator. A bubble detector may be provided with the hypodermic dosage measuring device, with or without the digital display and/or an audible indicator.

30 Claims, 7 Drawing Sheets

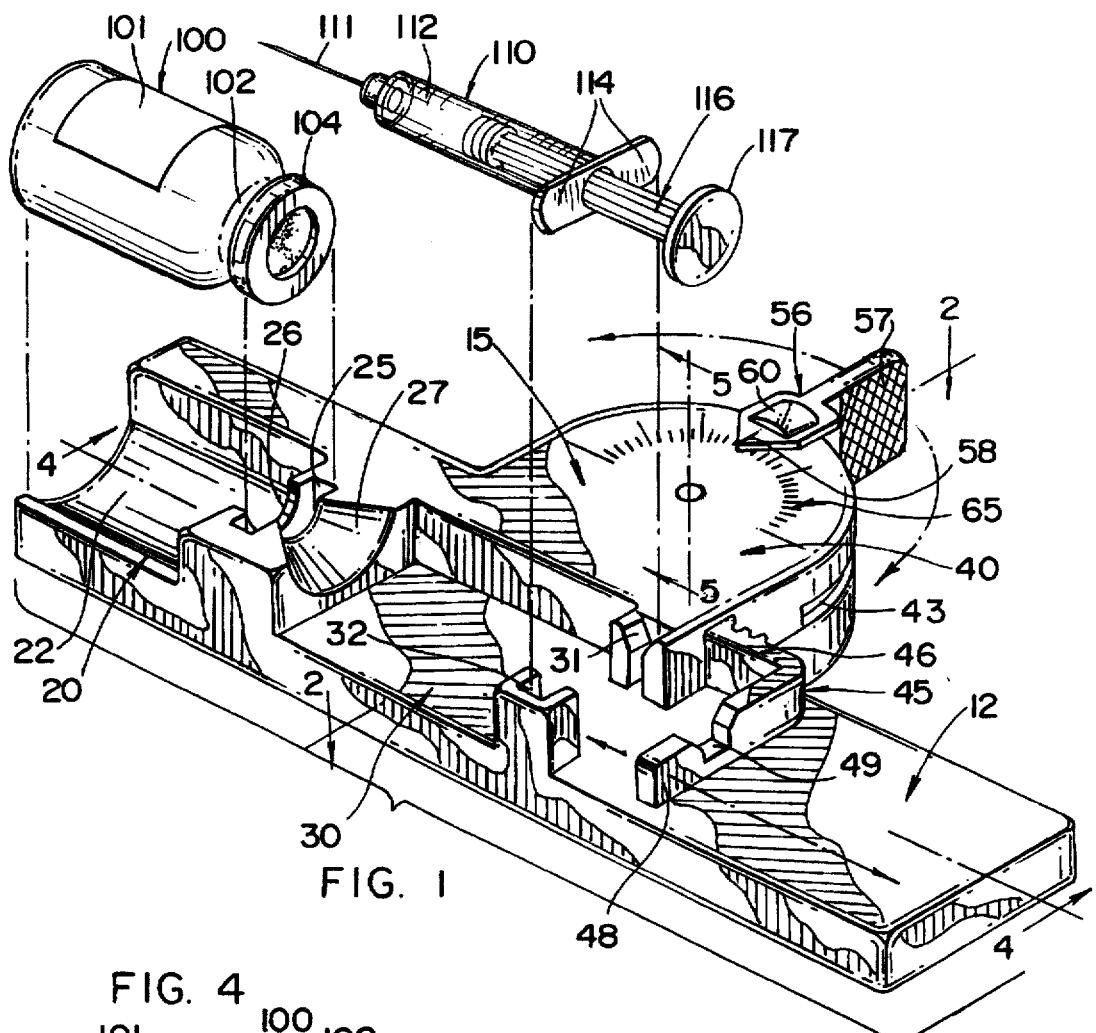
FIG. 1
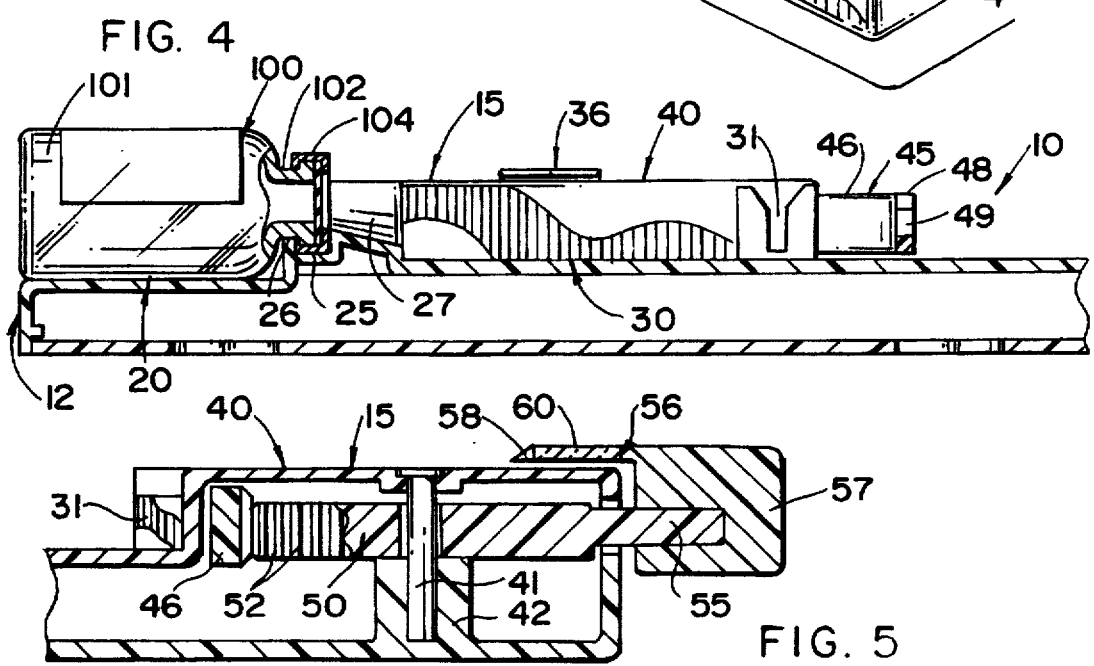
FIG. 4
FIG. 5

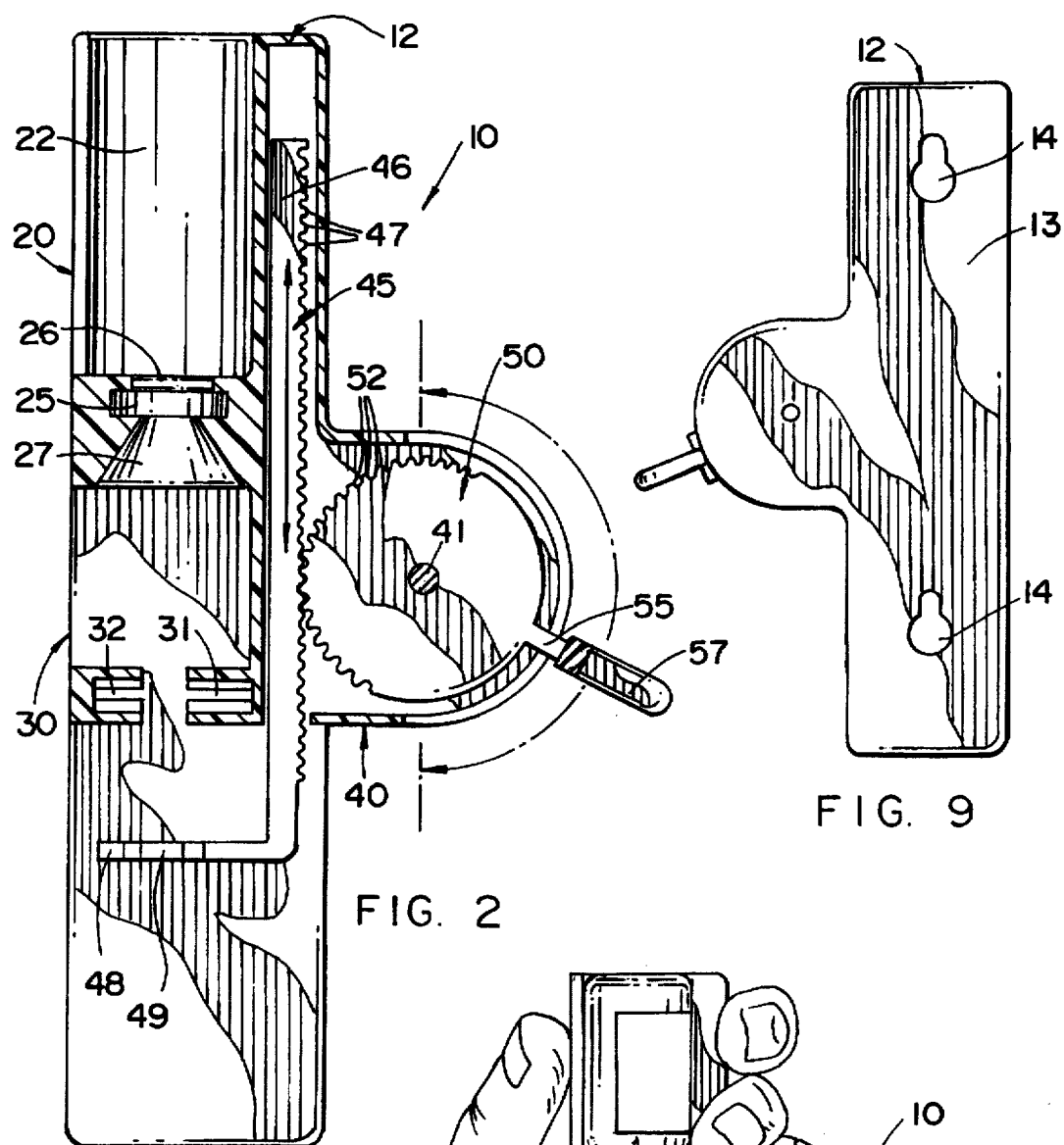
FIG. 2
FIG. 9
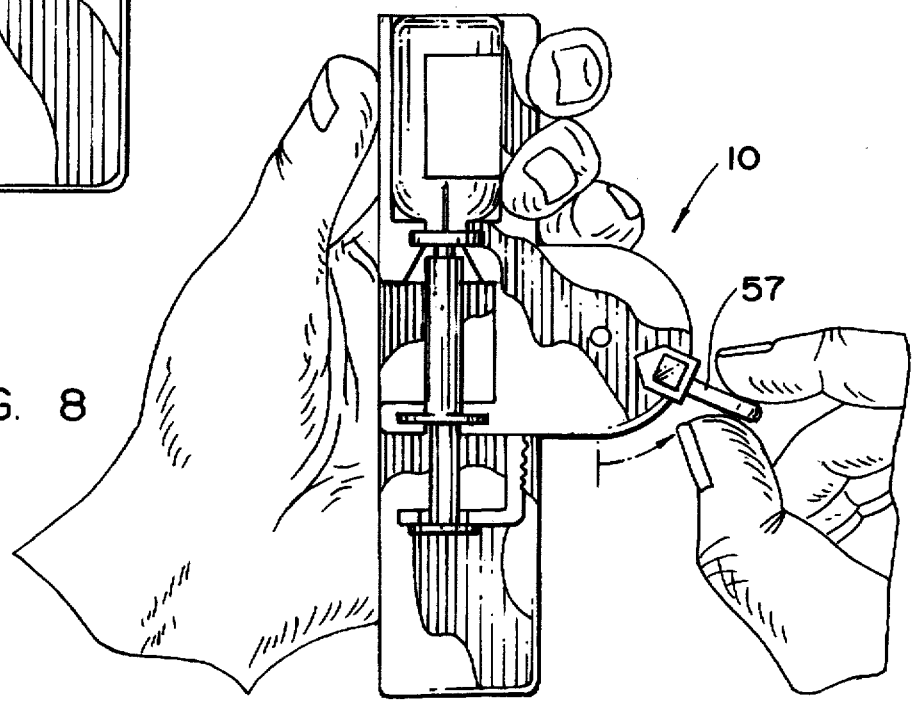
FIG. 8

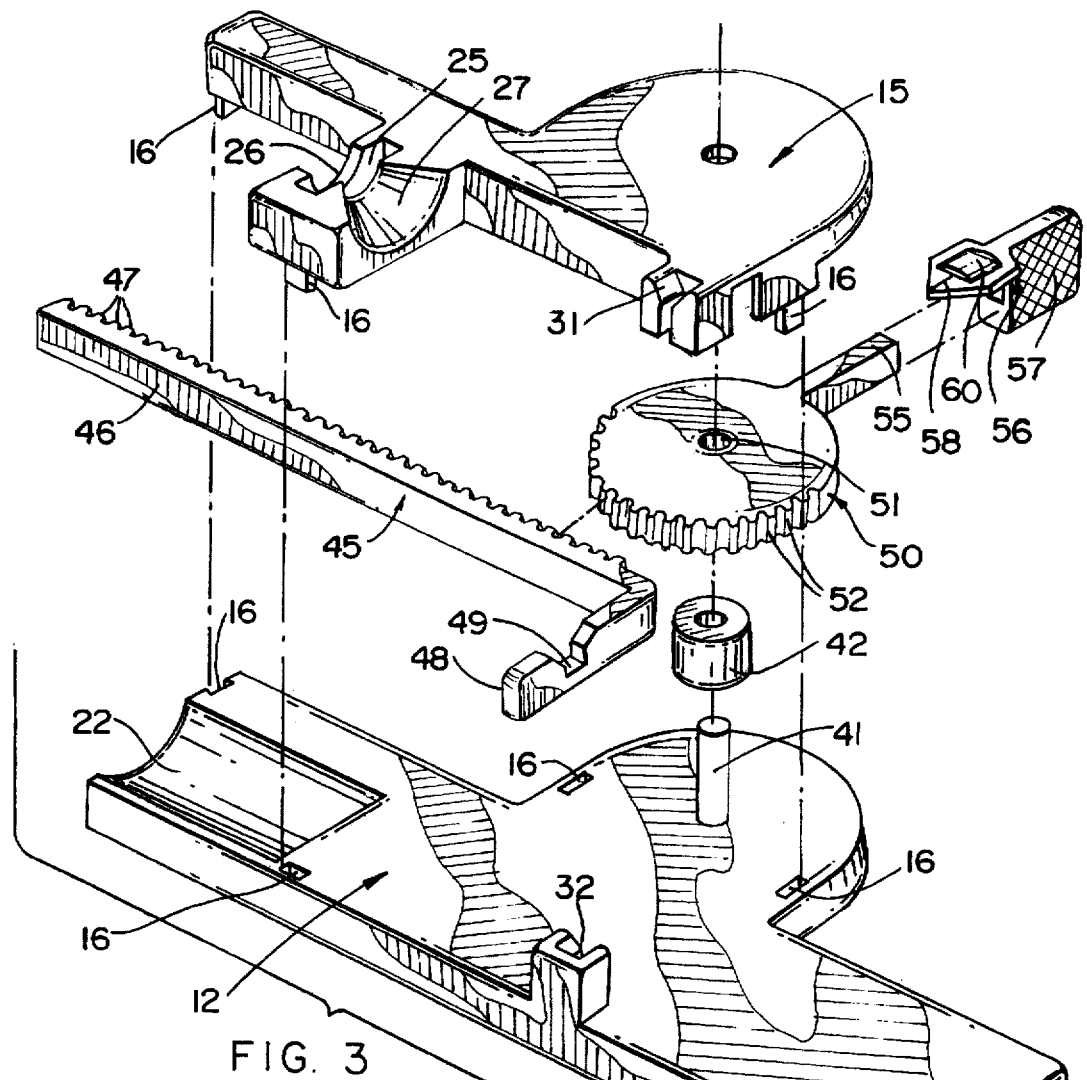
FIG. 3
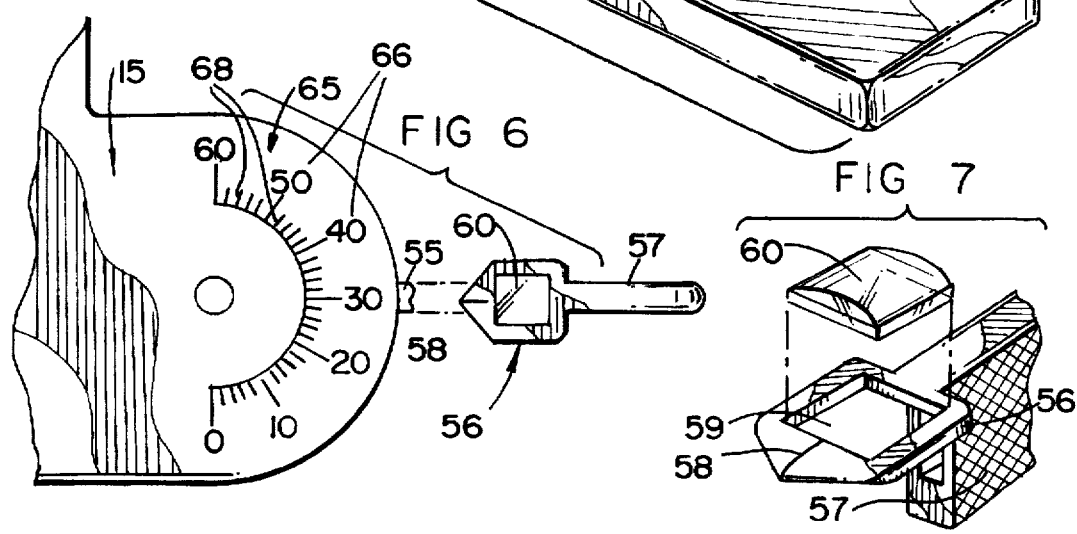
FIG. 6
FIG. 7

HYPODERMIC DOSAGE MEASURING DEVICE

BACKGROUND OF THE INVENTION

This application is related to application Ser. No. 08/161,461, maturing into U.S. Pat. No. 5,468,233 on Nov. 21, 1995, the disclosure of which is incorporated by reference herein in its entirety.

1. Field of the Invention

The present invention is relates to improvements in a hypodermic dosage measuring device adapted to enable accurate and facilitated measurement of precise doses of a drug to be administered by means of a hypodermic syringe. The improvements include, but are not limited, to one or more of the following: a hypodermic dosage measuring device including: an audible indicator to enable the user to hear an audible indication of the measured dose and/or a digital display to digitally indicate the measured dose and/or a bubble detector to indicate when bubbles are accidentally drawn into the measured dose.

2. Description of the Related Art

Hypodermic syringes are a widely used method of dispensing needed drugs to individuals. They are utilized by doctors, nurses, as well as patients and other lay persons in a variety of circumstances. In addition to the careful handling of the syringe, one of the most important responsibilities undertaken by an individual dispensing a drug utilizing a syringe is to assure that the appropriate dosage is administered. Because hypodermic syringes generally administer the drug directly in the bloodstream or in the tissue of the patient, the dosage quickly and directly affects the patient. As a result, it is very important to assure that the precise dosage is administered at all times.

Commonly, hypodermic syringes which come in standard sizes include a graduated scale disposed on the body of the syringe. Utilizing the scale, an individual administering the drug will draw a quantity of the drug from a vial into the syringe, and then expel quantities of the drug until the precise dosage is achieved. This common measurement procedure can often be difficult and time-consuming, and most importantly can be quite wasteful as a quantity of the drug is expelled in order to achieve the appropriate dosage. Further, individuals who are self-administering a drug often suffer from ailments that affect their eyesight or coordination, thereby making it difficult to use the scale effectively. Diminished eyesight and/or diminished dexterity of the user also increases the probability that the user will accidentally draw air bubbles into the measured dose, without recognizing the same, which can be very dangerous, and, at worst, fatal.

Because the scale is placed along a length of the syringe, the size of the numbers and scale is limited by the dimensions of the syringe such that larger, more easily read numbers cannot be implemented. As to the amount of the drug expelled, although it is seemingly small, due to the often expensive price of medication, even small amounts wasted over time can become quite costly.

In the past, there have been numerous devices adapted specifically for facilitating the measurement of the dosage drawn into a hypodermic syringe. These inventions include those disclosed in the references to Dobbins, U.S. Pat. No. 3,907,009, Ethington, U.S. Pat. No. 4,018,223, Right, U.S. Pat. No. 4,219,055, Maki, U.S. Pat. No. 4,252,159, LaDow, U.S. Pat. No. 4,778,454, Bloom, et al., U.S. Pat. No. 4,098,276, Strong, U.S. Pat. No. 4,883,101, Lee, U.S. Pat. No. 4,274,453, Waldbauer, Jr. et al., U.S. Pat. No. 3,833,030 and French, GB Patent No. 1,179,888. The majority of these references, which were designed primarily to assist individuals such as diabetics in self-administering a medication, employ a common method of providing for a measured dosage. Particularly, the syringe is placed in the device and the plunger of the syringe is manually pulled by the individual until it arrives at a point on a scale or until it arrives at a stopper which will not let the plunger move any further. Such a means of measuring the dosage, however, has difficulties associated with its effective use. Principally, since the individual must manually pull the plunger or manipulate small inconveniently disposed buttons, sick or handicapped individuals may have difficulties in grasping the plunger in its location within the dose measuring device, or may not be able to provide a smooth, fluid pulling motion which could result in inaccurate measurement. Also, the measuring devices which do not require the user to judge the scale provide a set stopping location. The set stopping location is only effective if the same dosage must always be taken, because otherwise an individual, often a sick or handicapped individual, must manipulate the complicated adjustment means provided to adjust the positioning of the stopper. The complicated adjustment of the stopper not only defeats the purpose of making the device easy to use by sick or handicapped individuals, but also makes the device ineffective to utilize in a hospital setting where many different kinds of drugs requiring many different dosages must be used. Even in the case of patients administering their own drug, multiple drugs may need to be dispensed, and dosages may be need to be varied depending on the condition of the individual.

With regard to Strong, U.S. Pat. No. 4,883,101, dosage indicating indicia are not provided on the measuring device to visually indicate an amount of drug drawn into a syringe. Nor does Strong disclose handle means extending from and fixed to a gear element, such that a position of the handle means relative to the indicating indicia visually indicates a relative position of a plunger engagement segment with respect to a vial holding portion. STRONG mentions that the device may be connected to a microprocessor controlled voice device to obtain a suitable readout indicating the amount of liquid medicinal uptake by the syringe.

Lee, U.S. Pat. No. 4,274,453 teaches an automated hematology analyzer with an input device that enables closed transfer of blood to the analyzer. Lee's device includes the provision of handle connected to a gear for manual manipulation of the gear. However, the transfer mechanism of LEE is provided with premeasured amounts of blood in vials to be extracted and transferred to the analyzer.

Accordingly, it would be highly beneficial to provide a dosage measuring device which will hold the drug vial and the syringe in a convenient dispensing location where they may rest until the syringe is precisely needed, which pulls the plunger automatically as part of the dosage measuring means, and which provides a clear, easy to view indication of the precise dosage dispensed for a variety of drugs requiring a variety of dosages. Optionally, for blind or visually impaired users, it would also be beneficial to provide non-visual means for indicating of the precise dosage dispensed for a variety of drugs requiring a variety of dosages. Still further, it would be beneficial to provide means for indicating the presence of air bubbles in the measured dosage. dispensed for a variety of drugs requiring a variety of dosages. The device of the present invention is designed specifically to meet these needs which remain in light of the related art.

SUMMARY OF THE INVENTION

The present invention is directed towards a hypodermic dosage measuring device. The dosage measuring device is adapted for use with a hypodermic syringe of the type including a needle, a dosage holding area, a flanged handle portion, and a plunger element slidably disposed within the dosage holding area. Further, the dosage measuring device may be utilized with conventional drug vials, the drug vials being of the type including a body to contain the drug, a neck, and a head portion through which the needle is inserted into the body of the vial for extracting the drug. The dose measuring device includes primarily a vial holding portion, a syringe holding portion, and a dose adjustment portion. The vial holding portion is specifically adapted to hold the head of the drug vial in a non-slidable position. The vial holding portion may also include a recess formed in the base thereof, which is adapted to receive the body of the drug vial thereon. Alternatively, or in addition thereto, the vial holding portion may include a sleeve for surrounding a protecting the vial from damage, should the user accidentally drop the device. The syringe holding portion, which is adapted to hold the hypodermic syringe in a drug extracting position, includes at least one channel member positioned to receive a side of the flanged handle portion of the syringe non-slidably therein. The channel member is spaced from the vial holding portion a sufficient distance such that the needle of the syringe is disposed within the vial when the vial is held in the vial holding portion and the handle portion of the syringe is held in the channel member. Included as part of the dose adjustment portion are an elongate, generally L-shaped plunger holder and a gear element. The plunger element has an elongated, toothed track segment adapted to slide in a longitudinal direction parallel to a length of the syringe. Extending perpendicularly from a proximal end of the tooth track segment is a plunger engagement segment. The plunger engagement segment is positioned to engage the plunger of the syringe such that longitudinal movement of the tooth track segment will result in corresponding longitudinal movement of the plunger. The longitudinal movement of the toothed track segment is controlled by the gear element. The gear element includes a plurality of teeth thereon and is positioned such that the teeth on the gear element engage the teeth on the track segment. Accordingly, movement of the gear element translates into corresponding movement of the track element. In order to facilitate movement of the gear element, a handle which is adapted to be held by a user when moving the gear element is provided to measure a dose.

In order to enable the amount of the drug dispensed to be precisely measured, indicating means are included. Also, means for detecting the presence of bubble in the measured dose may be included.

Specifically disclosed is a hypodermic dosage measuring device to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial; where the hypodermic dosage measuring device includes a vial holding portion connected to a syringe holding portion by a dose adjustment portion; the vial holding portion comprising a recess adapted to hold the head of the drug vial non-slidably therein; the syringe holding portion including at least one channel member for receiving a side of the flanged handle portion of the syringe non-slidably therein, and being sufficiently spaced from the vial holding portion such that the needle of the syringe is disposed within the vial upon the vial being positioned in the vial holding portion and the handle portion of the syringe being positioned in the channel member; the dosage adjustment portion further including a plunger engagement segment, for engaging a plunger of the syringe such that longitudinal movement of the dosage adjustment portion results in corresponding longitudinal movement of the plunger of the syringe, and a gear portion; a handle extending from and fixed to a gear element, wherein the gear element engages the gear portion to move the dosage adjustment portion in the longitudinal direction upon movement of the handle; and a digital display on the measuring device to visually and digitally indicate an amount of drug drawn into the syringe based on a position of the handle relative to the syringe holding portion.

The position of the handle of the hypodermic dosage measuring device relative to the syringe holding portion visually indicates a relative position of the plunger engagement segment with respect to the vial holding portion.

The gear element rotates about a centrally disposed axis post; and a potentiometer may be coaxially disposed with the gear element for outputting a signal having a voltage which is proportional to an amount of angular rotation of the gear element. A microprocessor is provided for receiving a signal outputted by the potentiometer. The microprocessor converts the voltage signal to a signal which is representative of a volume of fluid drawn into the syringe. The volume of fluid is proportional to the amount of angular rotation of the gear element. The microprocessor outputs a signal to the digital display. The digital display may comprise a liquid crystal display.

Further disclosed is an audible indicator on the measuring device to audibly indicate an amount of drug drawn into the syringe based on a position of the handle relative to the syringe holding portion. The audible indicator comprises a speaker (and, optionally, an earphone jack); an amplifier for driving the speaker (optionally, a volume control knob to control the output of the amplifier); and a voice chip for outputting signals representative of words to the amplifier. The microprocessor outputs a signal representative of a specific number which is in turn representative of a volume of fluid drawn into the syringe, with the volume of fluid being proportional to an amount of angular rotation of the gear element. The voice chip outputs signals representative of words to the amplifier, and the amplifier amplifies and outputs the signals to the speaker, whereupon the speaker outputs the words.

Further, a bubble detector may be provided on the measuring device to detect a presence of air bubbles in an amount of drug drawn into the syringe. The bubble detector includes a wave transmitter positioned on the measuring device on one side of the syringe, a wave receiver positioned opposite the wave transmitter on the metering device on a side of the syringe opposite the one side and a bubble detector amplifier. The wave receiver receives waves transmitted through the syringe and converts the waves to a signal representative of the contents of a medium within the syringe, and outputs a signal representative of the contents of a medium within the syringe to the bubble detector amplifier. The bubble detector amplifier amplifies and outputs the signal representative of the contents of a medium within the syringe to the microprocessor. The microprocessor analyzes the amplified signal and outputs a signal to the speaker to sound an alarm (e.g., an audible tone or voice) when the microprocessor determines the presence of bubbles.

Another example of a bubble detector is provided to include a wave transmitter positioned on the measuring device on one side of the syringe, a wave receiver positioned opposite the wave transmitter on the metering device on a side of the syringe opposite the one side and a bubble detector amplifier. The wave receiver receives waves transmitted through the syringe and converts the waves to a signal representative of the contents of a medium within the syringe, and outputs a signal representative of the contents of a medium within the syringe to the bubble detector amplifier. The bubble detector amplifier amplifies and outputs the signal representative of the contents of a medium within the syringe to the microprocessor. The microprocessor analyzes the amplified signal and outputs a signal to a digital display to digitally indicate the presence or absence of bubbles.

A preferred embodiment of the bubble detector includes an infrared light emitter positioned on one side of the syringe and an infrared receiver and transducer positioned on a side of the syringe opposite the one side. The infrared receiver and transducer receives infrared light transmitted through the syringe and outputs a signal indicative of the presence or absence of bubbles in the medium contained in the syringe. Still further, a preferred infrared light transmitter includes at least one light emitting diode.

Another embodiment of the hypodermic dosage measuring device includes a potentiometer disposed on the dosage adjustment portion so that a portion of the potentiometer is longitudinally moved with a longitudinal movement of the dosage adjustment portion. In this case, the potentiometer outputs a signal having a voltage which is proportional to an amount of longitudinal movement of the dosage adjustment portion. A microprocessor receives the voltage signal outputted by the potentiometer and converts it to a signal which is representative of a volume of fluid drawn into the syringe. The volume of fluid drawn into the syringe is proportional to the amount of longitudinal movement of the dosage adjustment portion. The microprocessor outputs this signal to the digital display.

Further disclosed is a hypodermic dosage measuring device to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial, wherein the hypodermic dosage measuring device includes a vial holding portion connected to a syringe holding portion by a dose adjustment portion. The vial holding portion includes a recess adapted to hold the head of the drug vial non-slidably therein. The syringe holding portion includes at least one channel member for receiving a side of the flanged handle portion of the syringe non-slidably therein, and is sufficiently spaced from the vial holding portion such that the needle of the syringe is disposed within the vial upon the vial being positioned in the vial holding portion and the handle portion of the syringe is positioned in the channel member. The dosage adjustment portion further includes a plunger engagement segment, for engaging a plunger of the syringe such that longitudinal movement of the dosage adjustment portion results in corresponding longitudinal movement of the plunger of the syringe, and a gear portion. A handle extends from and is fixed to a gear element. The gear element engages the gear portion to move the dosage adjustment portion in a longitudinal direction upon movement of the handle. An audible indicator is provided on the measuring device to audibly indicate an amount of drug drawn into the syringe based on a position of the handle relative to the syringe holding portion.

Still further, a potentiometer is coaxially disposed with the gear element for outputting a signal having a voltage which is proportional to an amount of angular rotation of the gear element. A microprocessor receives the voltage signal outputted by the potentiometer and converts the voltage signal to a signal which is representative of a specific number which is in turn representative of a volume of fluid drawn into the syringe. The volume of fluid drawn into the syringe is proportional to the amount of angular rotation of the gear element. The audible indicator further includes a speaker, an amplifier for driving the speaker and a voice chip for receiving the signals from the microprocessor and outputting signals representative of words to the amplifier. The voice chip outputs the signals representative of words to the amplifier and the amplifier amplifies and outputs the signals to the speaker. The speaker then outputs the words to indicate a volume which has been drawn into the syringe.

In addition to the audible indicator, a bubble detector may also be provided on the measuring device to detect a presence of air bubbles in the dosage holding area 112. The bubble detector includes a wave transmitter positioned on the measuring device on one side of the syringe and a wave receiver positioned opposite the wave transmitter on the metering device on a side of the syringe opposite the one side, and a bubble detector amplifier. The wave receiver receives waves transmitted through the syringe and converts the waves to a signal representative of the contents of a medium within the syringe, and outputs the signal to the bubble detector amplifier. The bubble detector amplifier amplifies and outputs the signal to a microprocessor. The microprocessor analyzes the amplified signal and outputs a signal to the speaker to sound an alarm when the microprocessor determines the presence of bubbles. Additionally, the microprocessor may output a signal to the speaker to sound an audible tone distinct from the alarm when the microprocessor determines the absence of bubbles. The position of the handle relative to the syringe holding portion visually indicates a relative position of the plunger engagement segment with respect to the vial holding portion.

In another embodiment, a hypodermic dosage measuring device is disclosed to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial, wherein the hypodermic dosage measuring device includes a vial holding portion connected to a syringe holding portion by a dose adjustment portion. The vial holding portion includes a recess adapted to hold the head of the drug vial non-slidably therein. The syringe holding portion includes at least one channel member for receiving a side of the flanged handle portion of the syringe non-slidably therein, and is sufficiently spaced from the vial holding portion such that the needle of the syringe is disposed within the vial upon the vial being positioned in the vial holding portion and the handle portion of the syringe is positioned in the channel member. The dosage adjustment portion further includes a plunger engagement segment, for engaging a plunger of the syringe such that longitudinal movement of the dosage adjustment portion results in corresponding longitudinal movement of the plunger of the syringe, and a gear portion. A handle extends from and is fixed to the gear element. The gear element engages the gear portion to move the dosage adjustment portion in the longitudinal direction upon movement of the handle. A bubble detector is provided on the measuring device to detect a presence of air bubbles in an amount of drug drawn into the syringe.

A microprocessor is contained within the measuring device and a speaker is mounted to the device. The bubble detector further includes a wave transmitter positioned on the measuring device on one side of the syringe, a wave receiver positioned opposite the wave transmitter, on the metering device, on a side of the syringe opposite the one side, and a bubble detector amplifier. The wave receiver receives waves transmitted through the syringe and converts the waves to a signal representative of the contents of a medium within the syringe, and outputs the signal to the bubble detector amplifier. The bubble detector amplifier amplifies and outputs the signal to the microprocessor. The microprocessor analyzes the amplified signal and outputs a signal to the speaker to sound an alarm (e.g., audible tone or voice) when the microprocessor determines the presence of bubbles. Additionally, the microprocessor may output a signal to the speaker to sound an audible tone or voice distinct from the alarm when the microprocessor determines the absence of bubbles.

In yet another embodiment, a hypodermic dosage measuring device includes a microprocessor contained within said device, a digital display and a bubble detector. The bubble detector includes a wave transmitter positioned on the measuring device on one side of a syringe, a wave receiver positioned opposite the wave transmitter on the metering device on a side of the syringe opposite the one side, and a bubble detector amplifier. The wave receiver receives waves transmitted through the syringe and converts the waves to a signal representative of the contents of a medium within the syringe, and outputs the signal to the bubble detector amplifier. The bubble detector amplifier amplifies and outputs the signal to the microprocessor. The microprocessor analyzes the amplified signal and outputs a signal to the digital display to digitally and visually indicate the presence or absence of bubbles. The wave transmitter preferably includes an infrared light emitter, and the wave receiver preferably includes an infrared receiver and transducer.

An object of the present invention is to provide a hypodermic dosage measuring device which will enable fast and consistently accurate measurement of precise doses of a drug to be dispensed by means of a syringe.

Another object of the present invention is to provide a hypodermic dosage measuring device which will enable sick, handicapped, and visually impaired individuals to quickly and easily measure out particular doses of a drug.

Yet another object of the present invention is to provide a hypodermic dosage measuring device which will ensure smooth and fluid motion of the plunger when drawing a drug into a syringe in a precise dosage.

A further object of the present invention is to provide a hypodermic dosage measuring device which will enable quick and facilitated measurement of varied dosages without requiring complex adaption or adjustment of the device.

Yet another object of the present invention is to provide a hypodermic dosage measuring device which can maintain the drug vial and hypodermic syringe in a convenient, ready to use position before and after the dosage is dispensed.

Another object of the present invention is to provide a hypodermic dosage measuring device which will not necessitate that an individual dispensing the specific dosage manually manipulate the plunger in order to pull it a desired amount.

Still another object of the present invention is to provide a hypodermic dosage measuring device which will minimize waste by eliminating the need to draw a quantity more than the dosage amount and later eliminate quantities until the dosage amount is reached.

Also an object of the present invention is to provide a dosage measuring device with which it is easy to read and/or hear the measurement value of a volume of drug drawn into the syringe.

A still further object of the invention is to provide a bubble detector which will readily alert even sick, handicapped, and/or visually impaired individuals to the presence of bubbles in the syringe.

BRIEF DESCRIPTION OF THE DRAWINGS

For a fuller understanding of the nature of the present invention, reference should be had to the following detailed description taken in connection with the accompanying drawings in which:

FIG. 1 is a perspective view of the dosage measuring device illustrating the positioning of the drug vial and hypodermic syringe therein;

FIG. 2 is a cross-sectional view of the dosage measuring device along line 2—2 of FIG. 1;

FIG. 3 is an exploded perspective view of the dosage measuring device;

FIG. 4 is a cross-sectional view along line 4—4 of FIG. 1;

FIG. 5 is a cross-sectional view along line 5—5 of FIG. 1;

FIG. 6 is a top plan view of the dosage adjustment portion illustrating the relation between the dosage indicating indicia and the indicator means;

FIG. 7 is an isolated, exploded view of the indicator means of the present invention;

FIG. 8 is a perspective view illustrating the functioning of the dosage measuring device of the present invention;

FIG. 9 is a rear view of the dosage measuring device showing an alternative embodiment;

Like reference numerals refer to like parts throughout the several views of the drawings.

DETAILED DESCRIPTION OF THE PREFERRED EMBODIMENTS

Figure 10:
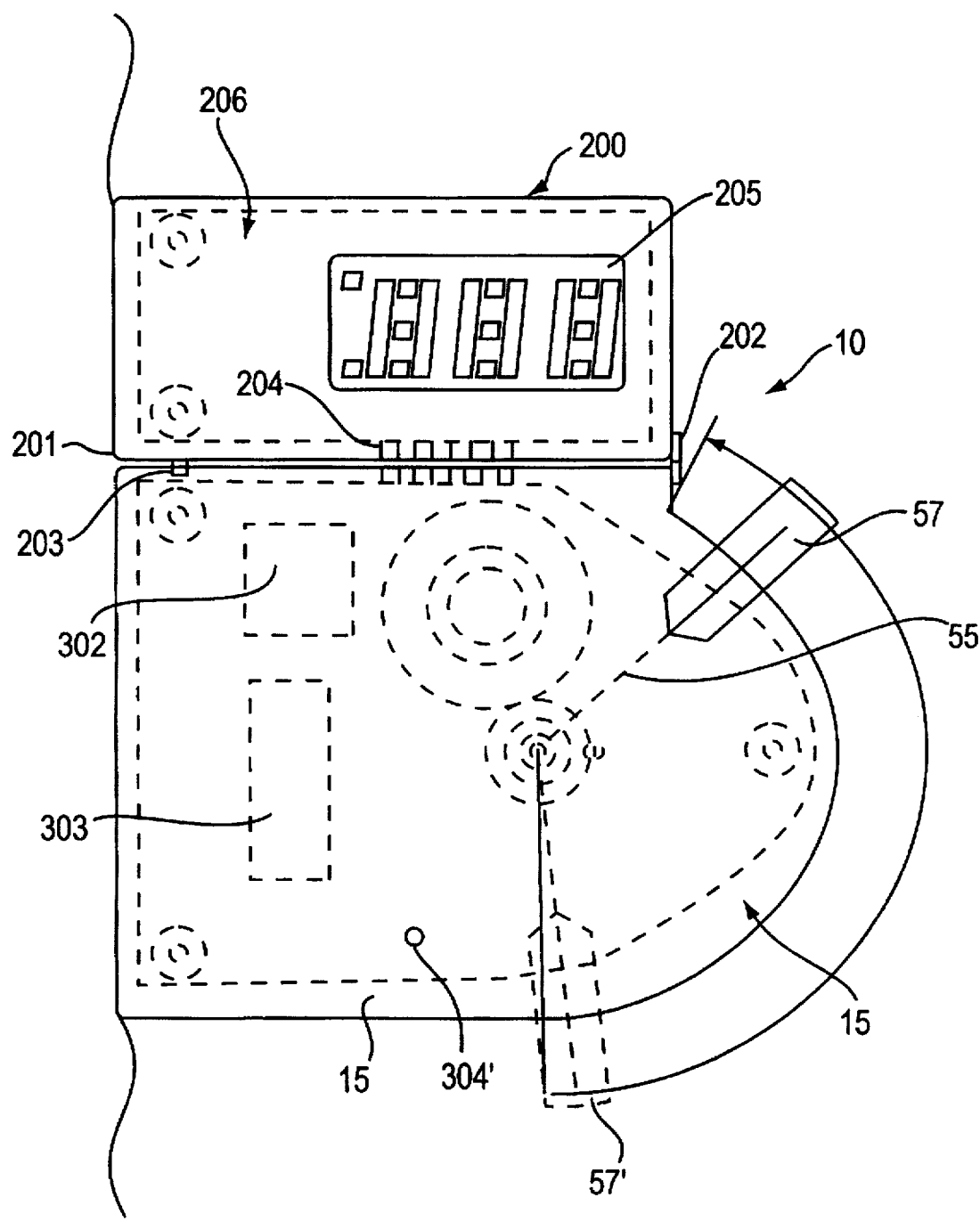
FIG. 10 is a top plan view of the dosage adjustment portion illustrating the LCD indicator and audio indicator according to the present invention.

Shown throughout FIGS. 1–14, the present invention is directed towards a hypodermic dosage measuring device, generally indicated as 10. The dosage measuring device 10 is adapted for use with a hypodermic syringe 110 of the type which includes a needle 111, a dosage holding area 112, a flanged handle portion 114, and a plunger element 116 which is slidably disposed within the dosage holding area 112. Specifically, standard hypodermic syringes 110 generally come in a finite number of sizes, a dispensing facility commonly utilizing the same size syringe 110 for a majority of its drug administrations. Further, the dosage measuring device 10 is adapted for use with a conventional drug vial 100. The drug vial 100 is preferably of the type having a body 101, which is usually rounded in configuration, a narrow neck 102, and a head portion 104 through which the needle 111 of the hypodermic syringe 110 is inserted into the body 101 in order to extract a dosage of a desired drug.

The hypodermic dosage measuring device 10, which is formed principally of a base 12 and an upper molded housing 15 includes primarily a vial holding portion 20, a syringe holding portion 30, and a dose adjustment portion 40. The vial holding portion 20 is adapted to hold the drug vial 100 non-slidably therein and in a preferred embodiment includes a recess 22 formed in the base 12 which is adapted to receive the body 101 of the drug vial thereon. Further, the vial holding portion 20 includes a molded collar 25, preferably, formed in the upper housing 15. The molded collar 25 is adapted to receive the head 104 of the drug vial 100 therein and includes a curved neck restraining area 26 wherever the neck 102 of the drug vial 100 fits. With the neck 102 held in place, the body 101 of the drug vial 100 extends towards the distal end of the base 12 and rests in the recess 22. Extending from a proximal side of the molded collar 25 is a molded guide area 27 adapted to enable facilitated positioning of the needle 111 of the hypodermic syringe 110 into the drug vial 100 through a center of the head 104.

Included as part of the syringe holding portion 30 is at least one channel member 31, but in the preferred embodiment, there are a pair of spaced channel members 31 and 32. A first of the channel members 31 is preferably molded as part of the housing 15, and a second of the channel members 32 is preferably molded as part of the base 12. The channel members 31 and 32 are spaced and positioned to receive the opposite sides of the flanged handle portion 114 of the syringe 110 therein. Further, the channel members 31 and 32 are positioned such that the syringe 110 will be held in a non-sliding position atop the hypodermic dosage measuring device 10 while the needle 111 of the syringe 110 extends through the head 104 of the drug vial 100 and into the body 101 of the drug vial 100 so as to extract a quantity of the drug therefrom. The particular size and spacing of the spaced channel members 31 and 32 relate to a standard hypodermic syringe 110 design. As there are a finite number of hypodermic syringe designs, and a single facility generally uses the same design hypodermic syringe for all of its uses, the channel members 31 and 32 are moldable in only a small number of differing orientations.

Turning to the dosage adjustment portion 40, it includes primarily an elongate, generally L-shaped plunger holder 45 and a gear element 50, both of which are adapted to be substantially contained between the upper molded housing 15 and the base 12. Specifically, the upper molded housing 15 and the base 12 are adapted to be secured to one another. Preferably, they are snap-fitted by means of a plurality of pegs and apertures 16 atop the base 12 however, any securing means such as glues and the like are also contemplated. The L-shaped plunger holder 45 includes an elongate track segment 46 having a plurality of teeth 47 thereon. The track segment 45 is disposed between the housing 15 and base 12 such that the teeth 47 confront the gear element 50 of the dose adjustment portion 40, and such that it will slide longitudinally, in a direction parallel to a length of the syringe 110. Further, a proximal end of the toothed track segment 46 is adapted to protrude from beneath the molded housing 15 upon a longitudinal sliding thereof. The plunger holder 45 also includes a plunger engagement segment 48 which extends perpendicularly from the proximal end of the track segment 46. This plunger engagement segment 48 remains exterior of the molded housing 15 and slides along the base 12 so as to move the plunger 116 of the syringe 110. The engagement segment 48 includes a collar portion 49, the collar portion 49 preferably including a channel adapted to receive a lip 117 of the plunger 116 therein. In the preferred embodiment, the lip 117 rests directly in the channel of the collar 49 such that longitudinal movement of the track segment 46 in either direction will result in corresponding longitudinal movement of the engagement segment 48, and accordingly movement of the plunger 116. Such positioning enables movement in both directions such that if too much of the drug is extracted, it can be returned to the vial. In an alternative embodiment, the collar 49 abuts the lip 117 of the plunger 116 such that only outward movement of the plunger 116 relative to the dosage holding area 111 is achieved. Further positioned between the base 12 and the housing 15 is the gear element 50. The gear element 50 is preferably round and includes a plurality of teeth 52 along the peripheral edge thereof which are adapted to engage the teeth 47 along the track segment 46. The gear element 50 is adapted to rotate about a central axis defined by an axis post 41 which preferably extends upwardly from the base 12. Preferably, a washer element 42 is first disposed over the axis post 41 to facilitate rotation of the gear element 50 which is disposed over the axis post 41 through a central opening 551. Extending from the gear element 50 is an elongated handle segment 55. The handle segment 55 is disposed so as to protrude from between the base 12 and molded housing 15 and facilitate actuation by a user. By sliding the elongate handle segment 55, the gear element 50 rotates, resulting in corresponding longitudinal movement of the plunger holder 45.

As seen in FIG. 6, positioned on an exterior surface of the molded housing 15, directly over the location of the gear element 50, are dosage indicating indicia 65. The dosage indicating indicia 65 may include a numbered scale 66, a graduated line scale 68, or a combination of both. The dosage indicating indicia 65 are specifically positioned so as to indicate an amount of the drug drawn into the syringe 110 from the drug vial 100, the amount being based on the position of the handle element 55 relative to the indicia 65. Also, because of the round configuration of the gear element 50 and the radial orientation of the handle segment 55, the indicia 65 can be made substantially larger merely by extending the handle segment 55 and increasing the size of the housing 15. In this manner, the size of the indicia is not limited by the size of the syringe 110. So as to further facilitate precise indication of the dosage drawn into the syringe 110, indicator means 56 are included over the handle segment 55.

Particularly, the indicator means 56 include a gripper area 57 adapted to be positioned over the end of the handle segment 55 to facilitate grasping of the handle segment 55 by a user. Extending over the handle segment 55, as part of the indicator means 56, is a pointer 58. The pointer 58 is adapted to be positioned directly on the molded housing 15 over the indicia 65 such that the point 58 indicates a precise dosage amount as indicated on the graduated line scale 68. In order to further assist viewing of the precise dosage, particularly for those individuals with impaired vision, the indicator means 56 includes a window opening 59 wherein a magnifying lens 60 can be positioned. This forms a magnified viewing slot adapted to pass directly over the numbered scale 66 of the dosage indicating indicia 65, thereby making the numerals easier to read and improving the ability of a user to determine the precise dosage amount. Accordingly, merely by sliding the handle segment 55 from its starting point with the indicator means 56 indicating zero dosage, a precise dosage will be drawn into the syringe 110, the precise dosage amount being limited only by the needs of the patient and not by a fixed stopper which only enables one dosage to be measured by the device.

In order to facilitate use in the hospital or like location, a dosage measuring device 10 can be adapted to be wall mounted, thereby making it convenient for frequent uses. In order to achieve this, the dosage measuring device 10 can include wall mounting means. Preferably, the wall mounting means are in the form of a pair of apertures 14 disposed in a rear surface 13 of the base 12, the openings 14 being adapted to receive a screw or nail, which has been secured to a wall, therein.

FIG. 10 is a top plan view of the dosage adjustment portion illustrating the LCD indicator and audio indicator according to the present invention. An indicator module 200 is removably attached to the main dosage measuring device 10. A preferred means of attaching the module 200 to the measuring device (i.e., main body) 10 is via the provision of two male plastic barbs 201 near one end of the module, and a plastic buckle 202 at the other end. The main body 10 is provided with female receptacles 203 for receiving the male barbs, and a mating half of the buckle 202. Of course, the male and female portions of the connections could be interchanged between the main body 10 and the module 200. Also, although this is a preferred way of attaching the module, any other equivalent connectors could be used to achieve the same function, e.g., velcro, metal buckles, snaps, etc. It is further noted that the main body 10 and module 200 could be formed as an integral unit, by integrally molding the two bodies as one unit.

A multi-pin connector 204 is provided between the main body 10 and module 200 to electrically connect the digital display 205 with the controller 302 contained in the main body. A male portion of the connector 204 is provided on the module 200 and a female portion is provided on the main body 10, or vice versa. The digital display is preferably in the form of an LCD, but other equivalents, e.g., an LED panel may be used.

Figure 11:
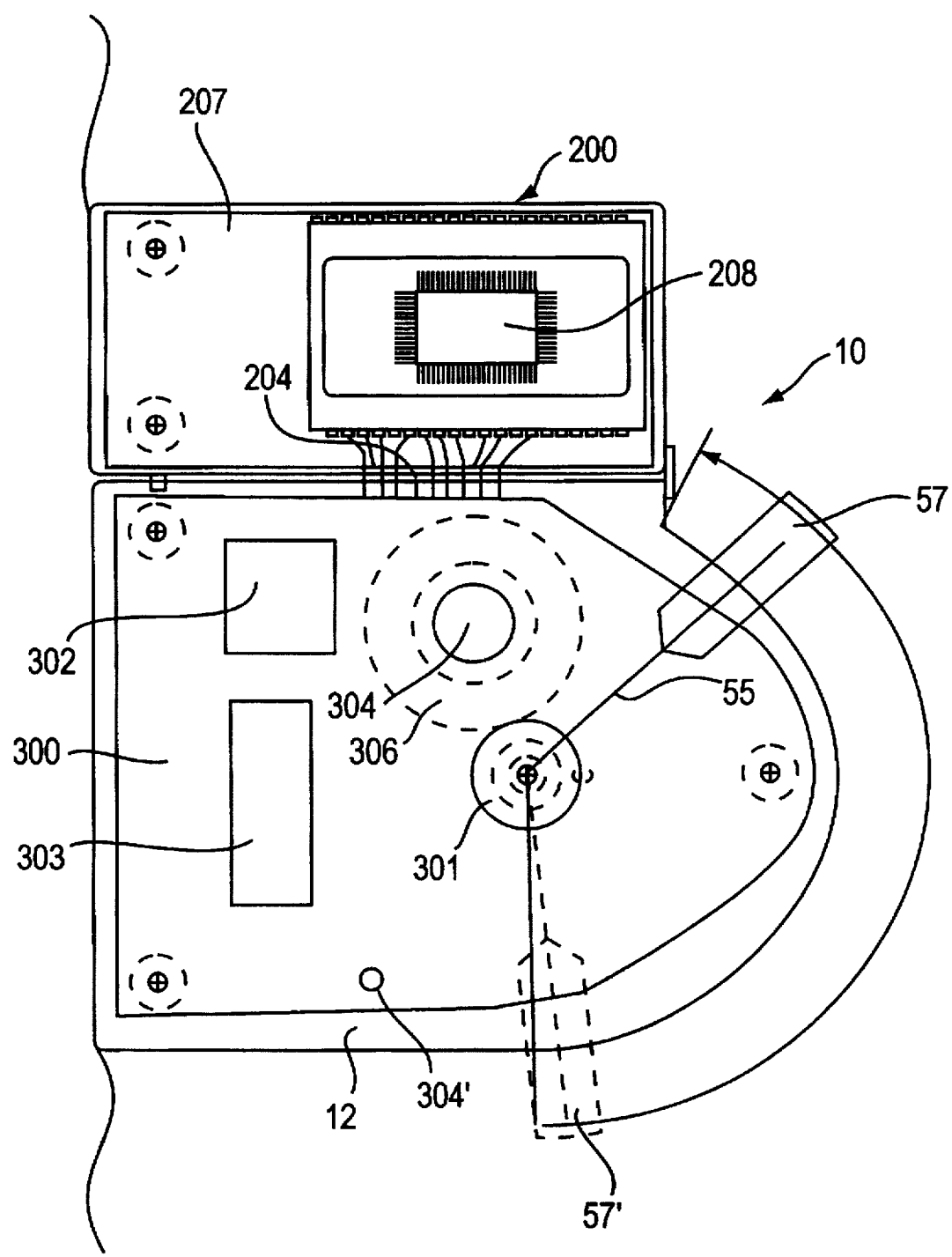
FIG. 11 is a top view of the dosage adjustment portion, LCD indicator and audio indicator of FIG. 10, with the top cover removed.
Figure 12:
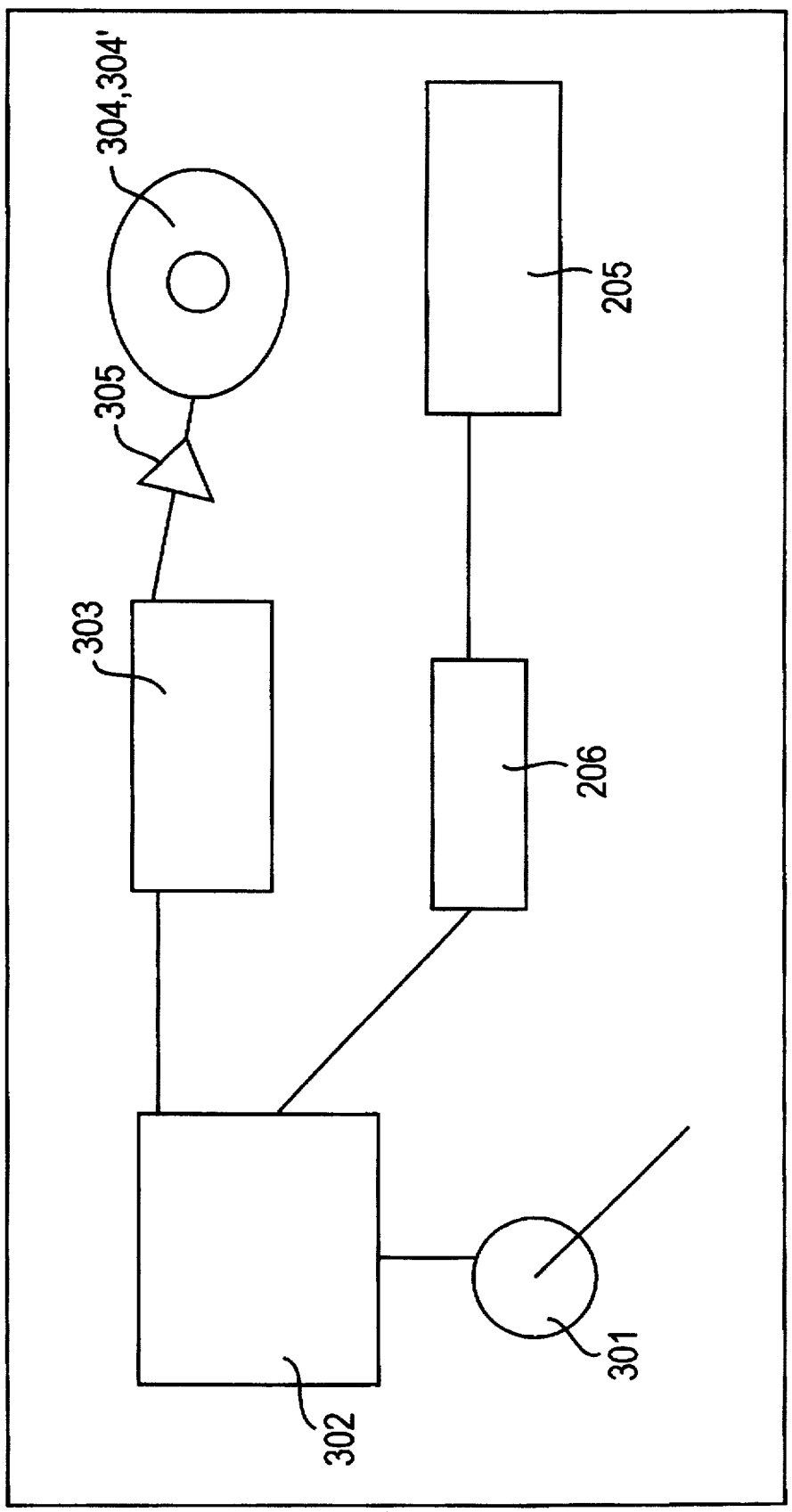
FIG. 12 is a schematic of the device shown in FIGS. 10 and 11, which explains the componentry thereof in further detail.

FIG. 11 shows the device of FIG. 10 with the upper housings 15 and 206, and digital display 205 removed. Note that the upper housing 206 is preferably a plastic molded housing made in a similar manner to housing 15. Directly beneath the position of the digital display, a driver chip 208 is mounted on a circuit board 207. In the preferred embodiment using an LCD display, chip 208 is an LCD chip. Intelligent or static LCD drivers may be used. A preferred LCD driver is the Hitachi HD61605 for static applications.

In the main body, a circuit board 300 is provided for supporting the controlling circuitry of the digital display. In a preferred embodiment, a potentiometer 301 (i.e., rotary pot) is provided to rotate coaxially with the gear element 50 about the central axis defined by the axis post 41. As the handle 57 is moved to rotate the gear element 50, the potentiometer includes a portion which moves therewith, and the potentiometer outputs a voltage signal which is representative of the angular displacement (i.e., sweep output) of the gear element. As noted above, the angular displacement of the gear element (and thus the handle 57) is proportional to the dosage amount drawn into the syringe. Accordingly, a volume amount of the dosage drawn into the syringe can be easily calculated from the output of the potentiometer. Preferably, the potentiometer is calibrated to a voltage range which varies between 0 and 5 volts, although any known end values can be used, as long as characteristics of the potentiometer and known and consistent. FIGS. 10 and 11 also show the handle at an opposite extreme end of its travel (57' in phantom).

In an alternative embodiment, a linear pot can be substituted for the rotary pot, as the potentiometer. In this case, the movable portion of the linear pot would be movable with the L-shaped plunger holder 45, and the output thereof would also directly correlated with the measured dosage.

In either case, the output voltage of the potentiometer is calibrated to be proportional to a measured stroke of the syringe plunger 116. The output voltage is inputted to an A/D converter contained within a microprocessor 302, as shown schematically in FIG. 12. A preferred microprocessor is the Motorola MC68HC11 with onboard A/D converter. However, there are many microprocessors available on the market which can be adapted for the specific functions required in this application.

The A/D converter converts the analog voltage signal received from the potentiometer 301 to a digital signal which is used by the microprocessor 302 to create a signal that corresponds to a number indicative of the number of volumetric units that have been drawn into the syringe. The microprocessor outputs this signal to the digital display driver 206, which processes the signal and outputs a control signal to the digital display so as to display a number indicating the volume of the dosage which has been taken up by the syringe.

Additionally, or in substitution therefore, an audible indicator may be provided with the dosage measuring device. The audible indicator includes a voice chip 303 and a speaker 304 which are electrically connected to the microprocessor 302 and potentiometer 301, as shown schematically in FIG. 12. The audible indicator operates as follows: the output voltage of the potentiometer is inputted to the A/D converter contained within microprocessor 302. The A/D converter converts the analog voltage signal received from the potentiometer 301 to a digital signal which is used by the microprocessor 302 to create a signal that corresponds to a number indicative of the number of volumetric units that have been drawn into the syringe.

The microprocessor then utilizes a look-up table to output specific addresses to the voice chip 303 that includes stored instructions for outputting signals to audibly produce words. The stored instructions in the voice chip 303 are for producing the words (numbers) zero through twenty (0–20), thirty (30), forty (40), fifty (50), sixty (60), seventy (70), eighty (80), ninety (90) and one hundred (100), etc. An algorithm is provided to concatenate the selected words to form the appropriate number (e.g., "twenty" "seven"). Please note that the voice chip may also be programmed with instructions for outputting signals to produce other words, and also may be programmed to output signals to produce words in foreign languages. The signals for producing the selected words are thus outputted by the voice chip 303 to an amplifier 305. The amplifier 305 outputs an amplified signal which drives the speaker 304 to audibly produce the selected words. In this manner, even a completely blind patient can still be apprised of the measured dose contained within the syringe.

Optionally, an ear phone jack 304' may be included in the audible indicator circuitry to allow a user to hear audible outputs from the device via an earphone, without outputting to the speaker 304, so as not to disrupt others in the immediate environment.

As is known, the amplifier 305 for the audible indicator circuit is preferably provided with a volume controller. The volume controller may be a rotary potentiometer or linear potentiometer for effecting the gain of the amplifier. All of the indicator systems disclosed herein are also preferably provided with an on/off switch for selectively providing power thereto. As one option, the on/off switch may be included with the volume controller. Another option is to provide a micro or optical switch element in the syringe holding portion, so that insertion of the syringe for taking a dose using the device will automatically actuate the switch to the "on" position. The device may further be provided with "time out circuitry", which is per se known, to either put the circuitry into a sleep mode, or completely switch off the circuitry after a predetermined period of non-use.

The power is preferably provided by a known battery arrangement, but may also include rechargeable batteries and a transformer that can use AC or DC voltage. Another option is to provide one or more solar cells on the device for providing power to operate and/or charge a rechargeable battery provided therewith. As one option, the on/off switch may be included with the volume controller.

As shown in FIG. 11, the speaker 304 is mounted on the bottom side of the circuit board 300 so that the speaker magnet 306 protrudes through a mounting hole therein. Holes or other like openings are provided on the lower housing of the measuring device, adjacent the speaker cone, to facilitate transmission of sound therethrough.

The microprocessor 302, voice chip 303 and potentiometer are preferably mounted on the top side of the circuit board 300. The amplifier 305 (not shown in FIG. 11) may be mounted on either side of the circuit board 300.

Figure 13:
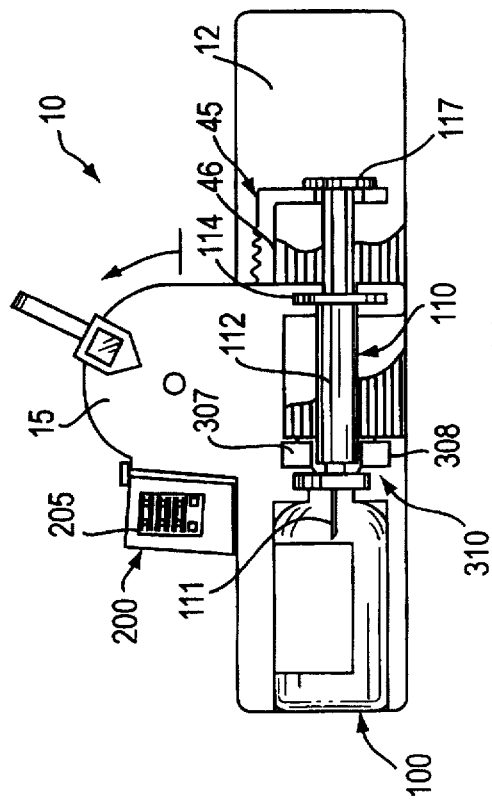
FIG. 13 is a top plan view of the present invention which includes the LCD indicator, audio indicator and bubble detector.
Figure 14:
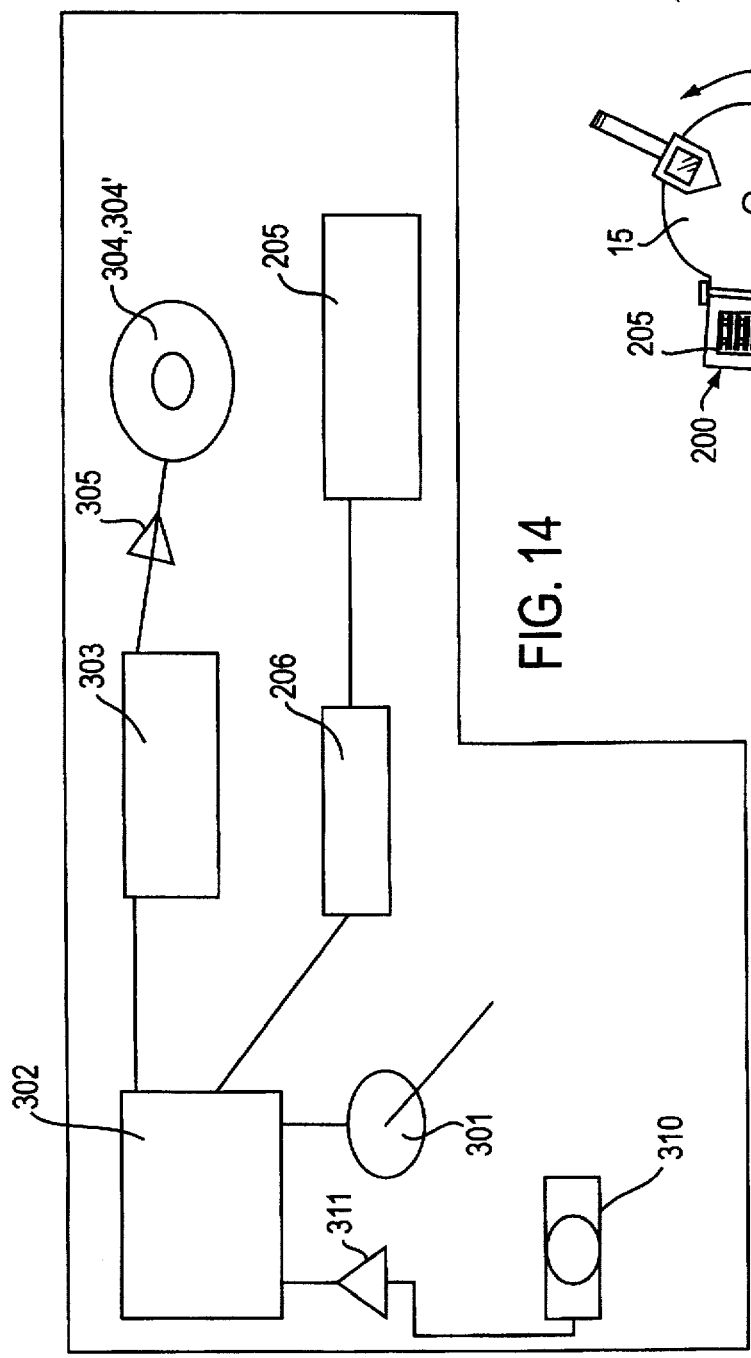
FIG. 14 is a schematic of the device shown in FIG. 13 which explains the componentry thereof in further detail.

FIG. 13 shows a further embodiment of the present invention in which a bubble detector 310 is also provided. Alternatively, the bubble detector 310 may be provided with only one of the digital and audio displays. Also, the bubble detector may be provided with those versions of the measuring device shown in FIGS. 1-9. The bubble detector 310 includes a wave transmitter 307 and a wave receiver 308. The wave transmitter 307 is mounted on one side of the syringe dosage holding area 112 for transmission of wave energy through the syringe and the contents thereof.

The wave receiver 308 is mounted on a side of the syringe holding area 112 opposite the wave transmitter 307. The wave receiver receives the waves transmitted through the syringe and its contents, and converts the waves received into an electronic signal. As shown schematically in FIG. 14, the bubble detector 310 (i.e., the wave receiver 308) transmits the converted signal to a bubble detector amplifier 311.

In a preferred embodiment, the wave transmitter transmits infrared light. Most preferably, the wave transmitter comprises one or more light emitting diodes. However, it is noted that it would be possible to use various ultrasonic emitters, visible light emitters, ultraviolet light emitters, and the like to accomplish the same function.

The wave receiver is adapted specifically to the type of wave energy that is transmitted by the wave transmitter. The wave receiver receives the waves after they pass through the syringe walls (i.e., in the vicinity of the syringe dosage holding area) and the contents of the syringe. The wave receiver includes a transducer which converts the received wave energy into an electrical signal which is proportional to the amount of wave energy received. On a scalar basis, when no bubbles are present in the dose, a transmission value of 1.0 is received by the wave receiver. When no dose is present, and the syringe dosage holding area is filled with air, the transmission value of waves received by the wave receiver is 0.8.

The bubble detector amplifier 311 receives the voltage signal from the wave receiver 308, amplifies the signal, and outputs it to the microprocessor 302. The microprocessor 302 is programmed to analyze the amplified signal, and makes a decision as to what level between the corresponding wave values of 0.8 and 1.0 that air content becomes an issue of concern. When the microprocessor makes a decision that air bubbles are present (i.e., when the transmission value of the waves received is between 0.8 and some predetermined cut-off value less than 1.0), the microprocessor outputs a signal to the external speaker (either through the voice chip or directly to the speaker) to drive an alarm sound which is output by the speaker, thereby warning the user that bubbles are present in the dose.

Optionally, the microprocessor can also be programmed to output a signal, which is distinct from the alarm signal, to the speaker to indicate that no bubbles are present (i.e., when the transmission value of the waves received is between the predetermined cut-off value and 1.0).

Additionally, or in lieu of sending audible signals, the microprocessor may output signals to the digital driver so as to drive the digital display to output visible readings indicating when bubbles are present and when they are not. Still further, if neither a digital display nor an audio indicator is included with the device, the microprocessor may simply output to a simple indicator light to alarm the user that bubbles are present.

Although the invention has been described with reference to particular means, materials and embodiments, it is to be understood that the invention is not limited to the particulars disclosed and extends to all equivalents within the scope of the claims.

What is claimed is:

1. A hypodermic dosage measuring device to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial; said hypodermic dosage measuring device comprising:

a vial holding portion connected to a syringe holding portion by a dose adjustment portion;

said vial holding portion comprising a recess adapted to hold the head of the drug vial non-slidably therein;

said syringe holding portion including at least one channel member for receiving a side of the flanged handle portion of the syringe non-slidably therein, and being sufficiently spaced from said vial holding portion such that the needle of the syringe is disposed within the vial upon the vial being positioned in said vial holding portion and the handle portion of the syringe being positioned in said channel member;

said dosage adjustment portion further including a plunger engagement segment, for engaging a plunger of the syringe such that longitudinal movement of said dosage adjustment portion results in corresponding longitudinal movement of the plunger of the syringe, and a gear portion;

a handle extending from and fixed to a gear element, wherein said gear element engages said gear portion to move said dosage adjustment portion in said longitudinal direction upon movement of said handle; and a digital display on said measuring device to visually and digitally indicate an amount of drug drawn into the syringe based on a position of said handle relative to said syringe holding portion.

2. A hypodermic dosage measuring device as recited in claim 1, wherein said gear element rotates about a centrally disposed axis post; said hypodermic measuring device further comprising:

a potentiometer substantially coaxially disposed with said gear element for outputting a signal comprising a voltage which is proportional to an amount of angular rotation of said gear element: and a microprocessor for receiving said signal comprising a voltage outputted by said potentiometer and converting said signal comprising a voltage to a signal which is representative of a volume of fluid drawn into the syringe, said volume of fluid being proportional to said amount of angular rotation of said gear element;

wherein said microprocessor outputs said signal to said digital display.

3. A hypodermic dosage measuring device as recited in claim 1, wherein said digital display comprises a liquid crystal display.

4. A hypodermic dosage measuring device as recited in claim 1, further comprising an audible indicator on said measuring device to audibly indicate an amount of drug drawn into the syringe based on a position of said handle relative to said syringe holding portion.

5. A hypodermic dosage measuring device as recited in claim 2, further comprising an audible indicator on said measuring device to audibly indicate an amount of drug drawn into the syringe based on a position of said handle relative to said syringe holding portion.

6. A hypodermic dosage measuring device as recited in claim 5, wherein said audible indicator comprises:

a speaker;

an amplifier for driving said speaker; and a voice chip for outputting signals representative of words to said amplifier;

wherein said microprocessor outputs a signal representative of a specific number which is in turn representative of a volume of fluid drawn into the syringe, said volume of fluid being proportional to said amount of angular rotation of said gear element;

wherein said voice chip outputs said signals representative of said words to said amplifier;

wherein said amplifier amplifies and outputs said signals representative of said words to said speaker; and wherein said speaker outputs said words.

7. A hypodermic dosage measuring device as recited in claim 6, wherein said audible indicator further comprises:

an ear phone jack to enable a user to receive outputs from said audible indicator via an ear phone.

8. A hypodermic dosage measuring device as recited in claim 1, further comprising:

a bubble detector on said measuring device to detect a presence of air bubbles in said amount of drug drawn into the syringe.

9. A hypodermic dosage measuring device as recited in claim 5, further comprising:

a bubble detector on said measuring device to detect a presence of air bubbles in said amount of drug drawn into the syringe.

10. A hypodermic dosage measuring device as recited in claim 6, further comprising:

a bubble detector on said measuring device to detect a presence of air bubbles in said amount of drug drawn into the syringe; said bubble detector comprising:

a wave transmitter positioned on said measuring device on one side of the syringe;

a wave receiver positioned opposite said wave transmitter on said metering device on a side of said syringe opposite said one side; and a bubble detector amplifier;

wherein said wave receiver receives waves transmitted through the syringe and converts said waves to a signal representative of the contents of a medium within the syringe, and outputs said signal representative of the contents of a medium within the syringe to said bubble detector amplifier;

wherein said bubble detector amplifier amplifies and outputs said signal representative of the contents of a medium within the syringe to said microprocessor;

wherein said microprocessor analyzes said amplified signal and outputs a signal to said speaker to sound an alarm when said microprocessor determines the presence of bubbles.

11. A hypodermic dosage measuring device as recited in claim 2, further comprising:

a bubble detector on said measuring device to detect a presence of air bubbles in said amount of drug drawn into the syringe; said bubble detector comprising:

a wave transmitter positioned on said measuring device on one side of the syringe;

a wave receiver positioned opposite said wave transmitter on said metering device on a side of said syringe opposite said one side; and a bubble detector amplifier;

wherein said wave receiver receives waves transmitted through the syringe and converts said waves to a signal representative of the contents of a medium within the syringe, and outputs said signal representative of the contents of a medium within the syringe to said bubble detector amplifier;

wherein said bubble detector amplifier amplifies and outputs said signal representative of the contents of a medium within the syringe to said microprocessor;

wherein said microprocessor analyzes said amplified signal and outputs a signal to said digital display to digitally indicate the presence or absence of bubbles.

12. A hypodermic dosage measuring device as recited in claim 8, wherein said bubble detector comprises:

an infrared light emitter positioned on one side of the syringe; and an infrared receiver positioned on a side of the syringe opposite said one side;

wherein said infrared receiver receives infrared light transmitted through the syringe and outputs a signal indicative of the presence or absence of bubbles in the medium contained in the syringe.

13. A hypodermic dosage measuring device as recited in claim 10, wherein said wave transmitter comprises an infrared light transmitter, and said wave receiver comprises an infrared light receiver and transducer.

14. A hypodermic dosage measuring device as recited in claim 13, wherein said infrared light transmitter comprises at least one light emitting diode.

15. A hypodermic dosage measuring device as recited in claim 1, further comprising:

a potentiometer disposed on said dosage adjustment portion so that a portion of said potentiometer is longitudinally moved with said longitudinal movement of said dosage adjustment portion;

wherein said potentiometer outputs a signal comprising a voltage which is proportional to an amount of longitudinal movement of said dosage adjustment portion; and a microprocessor for receiving said signal comprising a voltage outputted by said potentiometer and converting said signal comprising a voltage to a signal which is representative of a volume of fluid drawn into the syringe, said volume of fluid being proportional to said amount of longitudinal movement of said dosage adjustment portion;

wherein said microprocessor outputs said signal to said digital display.

16. A hypodermic dosage measuring device as recited in claim 1, wherein a position of said handle relative to said syringe holding portion visually indicates a relative position of said plunger engagement segment with respect to said vial holding portion.

17. A hypodermic dosage measuring device to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial; said hypodermic dosage measuring device comprising:

a vial holding portion connected to a syringe holding portion by a dose adjustment portion;

said vial holding portion comprising a recess adapted to hold the head of the drug vial non-slidably therein;

said syringe holding portion including at least one channel member for receiving a side of the flanged handle portion of the syringe non-slidably therein, and being sufficiently spaced from said vial holding portion such that the needle of the syringe is disposed within the vial upon the vial being positioned in said vial holding portion and the handle portion of the syringe being positioned in said channel member;

said dosage adjustment portion further including a plunger engagement segment, for engaging a plunger of the syringe such that longitudinal movement of said dosage adjustment portion results in corresponding longitudinal movement of the plunger of the syringe, and a gear portion;

a handle extending from and fixed to a gear element, wherein said gear element engages said gear portion to move said dosage adjustment portion in said longitudinal direction upon movement of said handle; and an audible indicator on said measuring device to audibly indicate an amount of drug drawn into the syringe based on a position of said handle relative to said syringe holding portion.

18. A hypodermic dosage measuring device as recited in claim 17, further comprising:

a potentiometer coaxially disposed with said gear element for outputting a signal comprising a voltage which is proportional to an amount of angular rotation of said gear element: and a microprocessor for receiving said signal comprising a voltage outputted by said potentiometer and converting said signal comprising a voltage to a signal which is representative of a specific number which is in turn representative of a volume of fluid drawn into the syringe, said volume of fluid being proportional to said amount of angular rotation of said gear element;

wherein said audible indicator further comprises:

a speaker;

an amplifier for driving said speaker; and a voice chip for receiving said signals from said microprocessor and outputting signals representative of words to said amplifier;

wherein said voice chip outputs said signals representative of said words to said amplifier;

wherein said amplifier amplifies and outputs said signals representative of said words to said speaker; and wherein said speaker outputs said words.

19. A hypodermic dosage measuring device as recited in claim 18, wherein said audible indicator further comprises:

an ear phone jack to enable a user to receive outputs from said audible indicator via an ear phone.

20. A hypodermic dosage measuring device as recited in claim 17, further comprising:

a bubble detector on said measuring device to detect a presence of air bubbles in said amount of drug drawn into the syringe.

21. A hypodermic dosage measuring device as recited in claim 18, further comprising:

a bubble detector on said measuring device to detect a presence of air bubbles in said amount of drug drawn into the syringe.

22. A hypodermic dosage measuring device as recited in claim 21, wherein said bubble detector further comprises:

a wave transmitter positioned on said measuring device on one side of the syringe;

a wave receiver positioned opposite said wave transmitter on said metering device on a side of said syringe opposite said one side; and a bubble detector amplifier;

wherein said wave receiver receives waves transmitted through the syringe and converts said waves to a signal representative of the contents of a medium within the syringe, and outputs said signal representative of the contents of a medium within the syringe to said bubble detector amplifier;

wherein said bubble detector amplifier amplifies and outputs said signal representative of the contents of a medium within the syringe to said microprocessor;

wherein said microprocessor analyzes said amplified signal and outputs a signal to said speaker to sound an alarm when said microprocessor determines the presence of bubbles.

23. A hypodermic dosage measuring device as recited in claim 22, wherein said microprocessor outputs a signal to said speaker to sound an audible tone distinct from said alarm when said microprocessor determines the absence of bubbles.

24. A hypodermic dosage measuring device as recited in claim 17, wherein a position of said handle relative to said syringe holding portion visually indicates a relative position of said plunger engagement segment with respect to said vial holding portion.

25. A hypodermic dosage measuring device to be utilized with a hypodermic syringe of the type including a needle, a dosage holding area, a flanged handle portion, and a plunger element slidably disposed therein, and a conventional drug vial having a body, a neck, and a head portion through which the needle is inserted into the body of the vial; said hypodermic dosage measuring device comprising:

a vial holding portion connected to a syringe holding portion by a dose adjustment portion;

said vial holding portion comprising a recess adapted to hold the head of the drug vial non-slidably therein;

said syringe holding portion including at least one channel member for receiving a side of the flanged handle portion of the syringe non-slidably therein, and being sufficiently spaced from said vial holding portion such that the needle of the syringe is disposed within the vial upon the vial being positioned in said vial holding portion and the handle portion of the syringe being positioned in said channel member;

said dosage adjustment portion further including a plunger engagement segment, for engaging a plunger of the syringe such that longitudinal movement of said dosage adjustment portion results in corresponding longitudinal movement of the plunger of the syringe, and a gear portion;

a handle extending from and fixed to a gear element, wherein said gear element engages said gear portion to move said dosage adjustment portion in said longitudinal direction upon movement of said handle; and a bubble detector on said measuring device to detect a presence of air bubbles in said amount of drug drawn into the syringe.

26. A hypodermic dosage measuring device as recited in claim 25, further comprising:

a microprocessor contained within said device; and a speaker mounted to said device;

wherein said bubble detector further comprises:
a wave transmitter positioned on said measuring device on one side of the syringe;
a wave receiver positioned opposite said wave transmitter on said metering device on a side of said syringe opposite said one side; and
a bubble detector amplifier;
wherein said wave receiver receives waves transmitted through the syringe and converts said waves to a signal representative of the contents of a medium within the syringe, and outputs said signal representative of the contents of a medium within the syringe to said bubble detector amplifier;

wherein said bubble detector amplifier amplifies and outputs said signal representative of the contents of a medium within the syringe to said microprocessor;
wherein said microprocessor analyzes said amplified signal and outputs a signal to said speaker to sound an alarm when said microprocessor determines the presence of bubbles.

27. A hypodermic dosage measuring device as recited in claim 26, wherein said microprocessor outputs a signal to said speaker to sound an audible tone distinct from said alarm when said microprocessor determines the absence of bubbles.

28. A hypodermic dosage measuring device as recited in claim 25, further comprising:

a microprocessor contained within said device; and a digital display;

wherein said bubble detector further comprises:
a wave transmitter positioned on said measuring device on one side of the syringe;
a wave receiver positioned opposite said wave transmitter on said metering device on a side of said syringe opposite said one side; and
a bubble detector amplifier;
wherein said wave receiver receives waves transmitted through the syringe and converts said waves to a signal representative of the contents of a medium within the syringe, and outputs said signal representative of the contents of a medium within the syringe to said bubble detector amplifier;
wherein said bubble detector amplifier amplifies and outputs said signal representative of the contents of a medium within the syringe to said microprocessor;
wherein said microprocessor analyzes said amplified signal and outputs a signal to said digital display to digitally and visually indicate the presence or absence of bubbles.

29. A hypodermic dosage measuring device as recited in claim 26, wherein wave transmitter comprises an infrared light emitter; and wherein said wave receiver comprises an infrared receiver and transducer.

30. A hypodermic dosage measuring device as recited in claim 28, wherein wave transmitter comprises an infrared light emitter; and wherein said wave receiver comprises an infrared receiver and transducer.

* * * * *